US011113736B1

(12) United States Patent
Hopkins (10) Patent No.: US 11,113,736 B1
(45) Date of Patent: Sep. 7, 2021

(54) METHOD, APPARATUS, AND COMPUTER PROGRAM PRODUCT FOR ESTIMATING INVENTORY BASED ON DISTRIBUTION DATA

(71) Applicant: McKesson Corporation, Irving, TX (US)

(72) Inventor: Stacy Hopkins, Tucker, GA (US)

(73) Assignee: MCKESSON CORPORATION, Irving, TX (US)

( * ) Notice: Subject to any disclaimer, the term of this patent is extended or adjusted under 35 U.S.C. 154(b) by 0 days.

(21) Appl. No.: 16/816,644

(22) Filed: Mar. 12, 2020

(51) Int. Cl.
| | |
|---|---|
| *G06Q 30/00* | (2012.01) |
| *G06Q 30/06* | (2012.01) |
| *G06N 5/04* | (2006.01) |
| *G16H 40/20* | (2018.01) |
| *G16H 20/10* | (2018.01) |
| *G06Q 10/08* | (2012.01) |

(52) U.S. Cl.
CPC ........... *G06Q 30/0605* (2013.01); *G06N 5/04* (2013.01); *G06Q 10/087* (2013.01); *G06Q 30/0607* (2013.01); *G06Q 30/0635* (2013.01); *G16H 20/10* (2018.01); *G16H 40/20* (2018.01)

(58) Field of Classification Search
None
See application file for complete search history.

(56) References Cited

U.S. PATENT DOCUMENTS

| | | | | |
|---|---|---|---|---|
| 8,099,339 B1* | 1/2012 | Pinsonneault | ......... | G06Q 40/08 705/28 |
| 8,626,529 B1* | 1/2014 | Pinsonneault | ......... | G16H 20/10 705/2 |
| 10,025,907 B1* | 7/2018 | Parker, Jr. | ............. | G16H 40/20 |
| 2003/0216974 A1* | 11/2003 | Browne | ............... | G06Q 10/087 705/28 |
| 2005/0283259 A1* | 12/2005 | Wolpow | ............... | G06Q 10/087 700/22 |
| 2013/0131862 A1* | 5/2013 | Jefferies | ................... | G07F 11/62 700/235 |
| 2014/0244281 A1* | 8/2014 | Smith | ..................... | G16H 20/10 705/2 |
| 2016/0342748 A1* | 11/2016 | Gulfo | ................... | G06Q 30/0639 |
| 2019/0333158 A1* | 10/2019 | Cedergreen | ............ | G16H 20/10 |
| 2019/0385722 A1* | 12/2019 | Wiley, II | ............ | G06Q 30/0633 |

* cited by examiner

*Primary Examiner* — Mila Airapetian
(74) *Attorney, Agent, or Firm* — Alston & Bird LLP (57) ABSTRACT

A method, apparatus and computer program product are provided for estimating inventory based on distribution data. A requesting computer may submit an order request (e.g., benefit request) indicating a product and merchant attributes. Inventory information of the merchant may not be accessible, so inventory information may be estimated based on distribution data relating to the distribution of product to the merchant. Estimates regarding quantities, high or low inventories, and/or the like may be made based on distribution history and/or estimated subsequent distributions. A prescriber computer, such as one used by a physician, may therefore receive estimated inventory information regarding prescription medication at various pharmacies, prior to submitting the prescription to a pharmacy.

18 Claims, 3 Drawing Sheets

METHOD, APPARATUS, AND COMPUTER PROGRAM PRODUCT FOR ESTIMATING INVENTORY BASED ON DISTRIBUTION DATA

TECHNOLOGICAL FIELD

Embodiments of the present invention relate generally to estimating inventory based on distribution data, and more particularly, to methods, apparatuses, and computer program products for providing inventory information to a requesting computer, based on distribution data.

BACKGROUND

During a patient encounter at a physician's office of other medical practice, a medical practitioner may discuss with the patient a potential prescription for medication. In some scenarios, a prescriber may submit a prescription to the patient's pharmacy. The patient may leave their appointment, to later learn that the pharmacy is not able to fill the prescription due to lack of available inventory or low inventory. The patient may then need to wait for the medication to become available, which in certain scenarios, may be detrimental to the patient's health. As another option, the patient may contact the medical practice and request the prescription be submitted to another pharmacy. Similar availability problems may continue to occur until the prescription is sent to a pharmacy that can fulfill the order. In certain scenarios one or several prescription transactions may need to be cancelled, and a confirmation of cancellation received from the pharmacy, before a new replacement prescription transaction can be submitted.

BRIEF SUMMARY

Methods, apparatuses, and computer program products are therefore provided for estimating inventory based on distribution data. According to example embodiments, a requesting computer (e.g., prescriber computer), may transmit a request for a specific product (e.g., prescription medication) to be obtained at a merchant (e.g., pharmacy), to a service provider computer. The service provider computer may not have access to the inventory information of the merchant, but may have access to certain distribution data relating to shipments of the product to the merchant, and/or upcoming shipments of the product. Example embodiments may therefore leverage the distribution data to estimate inventory at the merchant, and provide such estimates to the requesting computer.

An apparatus is provided, comprising at least one processor and at least one memory including computer program code. The at least one memory and the computer program code may be configured to, with the processor, cause the apparatus to at least receive, from a requesting computer, an indication of an order request comprising at least (a) a product identifier and (b) at least one merchant attribute describing at least one merchant at which the product is requested to be obtained. The at least one memory and the computer program code may be further configured to, with the processor, cause the apparatus to access distribution data relating to the distribution of the product to at least one merchant associated with the at least one merchant attribute. The at least one memory and the computer program code may be further configured to, with the processor, cause the apparatus to generate estimated inventory information, based on the distribution data, describing an estimated inventory of the product at at least one merchant associated with the at least one merchant attribute. The at least one memory and the computer program code may be further configured to, with the processor, cause the apparatus to transmit a message, comprising at least the estimated inventory information, to the requesting computer.

In certain embodiments, the at least one merchant attribute is a merchant identifier of the merchant at which the product is requested to be obtained, and/or the at least one merchant attribute describes a geographic area of the merchant at which the product is requested to be obtained.

In certain embodiments, the requesting computer is a prescriber computer, the order request comprises a benefit request, the product identifier identifies a prescribed medication, and the at least one merchant attribute describes a pharmacy at which the prescribed medication is requested to be obtained.

The at least one memory and the computer program code may be further configured to, with the processor, cause the apparatus to determine the estimated inventory information reflects an estimated inventory that has a first predetermined relationship with a predetermined threshold. The at least one memory and the computer program code may be further configured to, with the processor, cause the apparatus to in response to determining the estimated inventory has the first predetermined relationship with the predetermined threshold, identify an alternative merchant determined to have a second predetermined relationship with the predetermined threshold, wherein the message further comprises an indication of the alternative merchant.

In certain embodiments, the distribution data comprises at least one of a last distribution date and average distribution frequency, and the estimated inventory information is determined based on at least the last distribution date and the average distribution frequency.

The at least one memory and the computer program code may be further configured to, with the processor, cause the apparatus to cause display of the message at the requesting computer.

A method is also provided, including, receiving, from a requesting computer, an indication of an order request comprising at least (a) a product identifier and (b) at least one merchant attribute describing at least one merchant at which the product is requested to be obtained, and accessing distribution data relating to the distribution of the product to at least one merchant associated with the at least one merchant attribute. The method may further include generating estimated inventory information, based on the distribution data, describing an estimated inventory of the product at at least one merchant associated with the at least one merchant attribute, and transmitting a message, comprising at least the estimated inventory information, to the requesting computer.

The method may further include determining the estimated inventory information reflects an estimated inventory that has a first predetermined relationship with a predetermined threshold, and in response to determining the estimated inventory has the first predetermined relationship with the predetermined threshold, identifying an alternative merchant determined to have a second predetermined relationship with the predetermined threshold, wherein the message further comprises an indication of the alternative merchant. In certain embodiments, the method includes causing display of the message at the requesting computer.

A computer program product is also provided, the computer program product comprising at least one non-transitory computer-readable storage medium having computer-executable program code instructions stored therein, the computer-executable program code instructions comprising program code instructions to receive, from a requesting computer, an indication of an order request comprising at least (a) a product identifier and (b) at least one merchant attribute describing at least one merchant at which the product is requested to be obtained. The computer-executable program code instructions may further include program code instructions to access distribution data relating to the distribution of the product to at least one merchant associated with the at least one merchant attribute. The computer-executable program code instructions may further include program code instructions to generate estimated inventory information, based on the distribution data, describing an estimated inventory of the product at at least one merchant associated with the at least one merchant attribute. The computer-executable program code instructions may further include program code instructions to transmit a message, comprising at least the estimated inventory information, to the requesting computer.

The computer-executable program code instructions may further include program code instructions to determine the estimated inventory information reflects an estimated inventory that has a first predetermined relationship with a predetermined threshold.

The computer-executable program code instructions may further include program code instructions to in response to determining the estimated inventory has the first predetermined relationship with the predetermined threshold, identify an alternative merchant determined to have a second predetermined relationship with the predetermined threshold, wherein the message further comprises an indication of the alternative merchant.

In certain embodiments, the apparatus the method, and/or the computer program product do not have access to actual inventory information of the at least one merchant.

An apparatus is also provided, including, means for receiving, from a requesting computer, an indication of an order request comprising at least (a) a product identifier and (b) at least one merchant attribute describing at least one merchant at which the product is requested to be obtained. The apparatus further includes means for accessing distribution data relating to the distribution of the product to at least one merchant associated with the at least one merchant attribute. The apparatus further includes means for generating estimated inventory information, based on the distribution data, describing an estimated inventory of the product at at least one merchant associated with the at least one merchant attribute, and means for transmitting a message, comprising at least the estimated inventory information, to the requesting computer.

The apparatus may further include means for determining the estimated inventory information reflects an estimated inventory that has a first predetermined relationship with a predetermined threshold, and in response to determining the estimated inventory has the first predetermined relationship with the predetermined threshold, identifying an alternative merchant determined to have a second predetermined relationship with the predetermined threshold, wherein the message further comprises an indication of the alternative merchant. In certain embodiments, the apparatus includes means for causing display of the message at the requesting computer.

The above summary is provided merely for purposes of summarizing some example embodiments of the invention so as to provide a basic understanding of some aspects of the invention. Accordingly, it will be appreciated that the above described example embodiments are merely examples and should not be construed to narrow the scope or spirit of the disclosure in any way. It will be appreciated that the scope of the disclosure encompasses many potential embodiments, some of which will be further described below, in addition to those here summarized.

BRIEF DESCRIPTION OF THE SEVERAL VIEWS OF THE DRAWINGS

Having thus described embodiments of the invention in general terms, reference will now be made to the accompanying drawings, which are not necessarily drawn to scale, and wherein:

DETAILED DESCRIPTION

Some embodiments of the present invention will now be described more fully hereinafter with reference to the accompanying drawings, in which some, but not all embodiments of the invention are shown. Indeed, various embodiments of the invention may be embodied in many different forms and should not be construed as limited to the embodiments set forth herein; rather, these embodiments are provided so that this disclosure will satisfy applicable legal requirements. Like reference numerals refer to like elements throughout.

As used herein, where a computing device is described to receive data from another computing device, it will be appreciated that the data may be received directly from the other computing device and/or may be received indirectly via one or more intermediary computing devices, such as, for example, one or more servers, relays, routers, network access points, and/or the like. Similarly, where a computing device is described herein to transmit data to another computing device, it will be appreciated that the data may be sent directly to the other computing device or may be sent to the other computing device via one or more interlinking computing devices, such as, for example, one or more servers, relays, routers, network access points, and/or the like.

Figure 1:
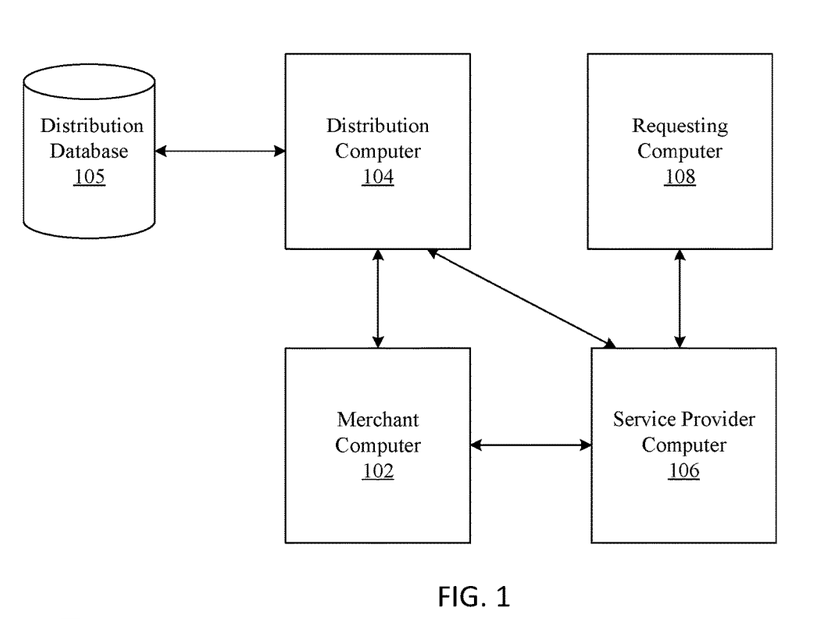
FIGS. 1 and 2 are example overviews of systems that can be used to practice some example embodiments described herein.

FIG. 1 is an overview of a system that can be used to estimate inventory based on distribution data, according to certain example embodiments described herein.

A merchant computer 102 may be associated with a merchant, retailer, and/or the like, and may be configured to transmit distribution requests for additional product to the distribution computer 104. In certain examples, the merchant computer 102 may be configured to submit such distribution requests to the service provider computer 106, which may in turn provide the distribution requests to the distribution computer 104. In any event, the distribution computer 104 may be configured to process and/or route the distribution requests such that shipment of the desired product and quantity is distributed to the merchant either immediately, and/or at a scheduled day and time, for example. In certain embodiments, the distribution requests may be submitted on an as-needed basis. In certain embodiments, an inventory system of the merchant computer 102 may generate a distribution request when the inventory of a specific product is low (e.g., at or below a specific threshold), or zero. As another example, the distribution request may be configured to be repeated and fulfilled on a regular time interval, such that the merchant computer 102 does not necessarily send a distribution request for each instance of a requested distribution. For example, the distribution computer 104 may automatically initiate distribution of 100 units of the same product on the first of each month.

The distribution computer 104 may store information pertaining to the distribution requests as distribution data in distribution database 105, which may include any memory device, database, and/or the like. The distribution data of distribution database 105 may comprise historical distribution data, including information describing repeat distribution requests, and/or distribution requests placed on an as-needed basis. The distribution data of distribution database 105 may further comprise information relating to upcoming shipments, such as to fulfill distribution requests recently placed but not yet fulfilled. An example record stored as distribution data may include a merchant identifier identified as the recipient merchant of the shipment, item or product identifier, quantity, date of distribution request generation, date of shipment, and/or the like. The merchant identifier may have further information associated therewith, such as an address and/or location of the merchant.

The requesting computer 108 may be associated with any business entity desiring information regarding the inventory information of a merchant, (such as a merchant associated with merchant computer 102), but that may not have access to the merchant computer 102, and/or may not have access to real-time, near real-time, and/or actual inventory information of the merchant. The requesting computer 108 may be configured to transmit to the service provider computer 106, an order request representing a request for a particular product, and a merchant attribute describing a merchant at which the product is requested to be obtained or purchased.

The service provider computer 106 may include, but is not limited to, a processor-driven device that is configured for receiving, processing, and responding to order requests from the requesting computer 108. Additionally or alternatively, the service provider computer 106 may be operable to facilitate the receipt, routing, and/or processing of order requests and/or associated responses amongst various components and/or subsystems such as, but not limited to, those depicted in FIGS. 1 and 2.

In certain exemplary embodiments, the service provider computer 106 may be configured as or may comprise a switch or router that evaluates, modifies, reformats, generates, and/or routes the order requests received from the requesting computer 108. The service provider computer 106, associated computer program products, methods, and/or apparatuses may not have access to the merchant computer 102, and/or may not have access to real-time, near real-time, and/or actual inventory information of the merchant. As such, the service provider computer 106 may access distribution data relating to the distribution of product to various merchants, estimate information regarding inventory at a particular merchant, modify the order request to include information regarding the estimated inventory, and return a response to the requesting computer 108. As such, the service provider computer 106 may reformat orders into another form of transaction and modify the recipient information of the reformatted order before routing the reformatted transaction to another party, such as the requesting computer 108. The service provider computer 106 may also optionally apply edits to at least some of the orders and/or transactions.

In certain embodiments, the service provider computer 106 may comprise or embody the distribution computer 104, such that the service provider computer 106 may access the distribution data of distribution database 105 to estimate inventory information pertaining to various merchants.

Figure 2:
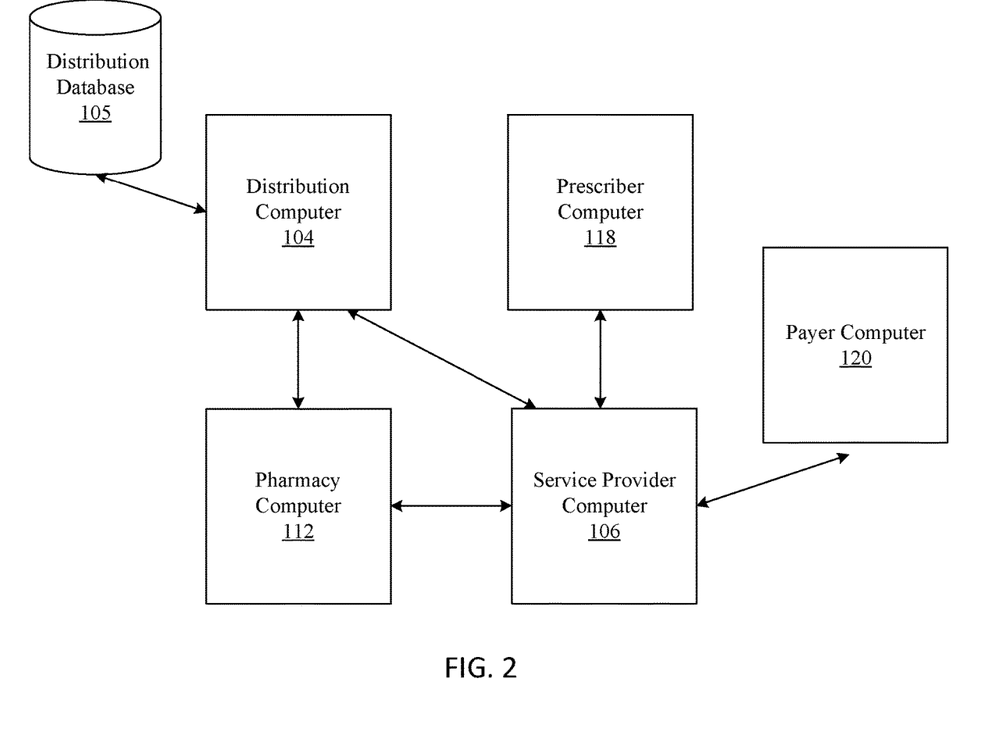

FIG. 2 is an overview of a system that can be used to estimate inventory information of prescription medication at a pharmacy, based on distribution data, according to certain example embodiments described herein. The system of FIG. 2 is an exemplary variation of the system of FIG. 1, and may be employed according to example embodiments.

In the exemplary system of FIG. 2, the merchant computer 102 may be embodied by or may comprise a pharmacy computer 112. In this regard, the merchant computer 102 and/or pharmacy computer 112 may be associated with a pharmacy, and may transmit distribution requests for prescription medication to the distribution computer 104. As such, a distribution request may comprise a merchant (e.g., pharmacy) identifier identifying a recipient merchant (e.g., pharmacy), item or product (e.g., prescription medication) identifier (such as but not limited to a National Drug Code (NDC)), quantity, unit of measure, date of distribution request generation, date of shipment, and/or the like.

The pharmacy computer 104 may be associated with a pharmacy or pharmacy network to transmit distribution requests for distribution of prescription medication, and/or the like. The pharmacy computer 104 may additionally or alternatively be associated with a physician's office, clinic, long-term care facility, hospital, etc. Accordingly, while the exemplary pharmacy computer 104 may be frequently referenced herein as part of a pharmacy or pharmacy network, the pharmacy computer 104 may be associated with any other healthcare provider, such as a physician's office, hospital and/or other medical facility.

According to certain embodiments, the pharmacy computer 104 may optionally facilitate the submission of prescription transaction requests made by patients or consumers and the communication of information associated with prescription transactions to the service provider computer 106. In certain example embodiments, the pharmacy computer 104 may be a point of sale device associated with a pharmacy. The execution of the computer-implemented instructions by the pharmacy computer 104 may facilitate the submission of pharmacy transaction requests made by patients, pharmacists, and/or the like, and the communication of information associated therewith to a service provider computer 106.

Accordingly, in certain embodiments, the service provider computer 106 may be further configured to receive and process prescription transactions received from the pharmacy computer 112 and/or the payer computer 120 (described below), relating to prescription tracking, claims processing, benefits, billing, other healthcare transactions, and/or other related activities.

In certain exemplary embodiments, the service provider computer 106 may be configured as or may comprise a switch or router that evaluates, modifies, reformats, generates, and/or routes healthcare transactions. For example, the service provider computer 106 may process orders communicated from the pharmacy computer 112 to a payer computer 120, such as that associated with a pharmacy benefits manager (PBM), an insurer, a Medicare or other government healthcare insurance program payer, or other payer. According to certain embodiments, the payer computer 120 may comprise any other computer system that receives and adjudicates a prescription transaction on behalf of the payer.

As such, the requesting computer 108 may be embodied by or may include a prescriber computer 118, that facilitates entry of prescription details made by physicians and/or the like, and the communication of information associated therewith to the service provider computer 106. The prescriber computer 118 may be associated with a healthcare provider, such as an entity that may prescribe medication and/or treatments, for example, a physician's office, clinic, long-term care facility, hospital, etc. While the exemplary prescriber computer 118 may be frequently referenced herein as part of a physician's office or healthcare network, the prescriber computer 118 may be associated with any other healthcare provider, such as a hospital, urgent care center, dentist, and/or other medical facility. A physician and/or the like may enter details pertaining to a prescription during a patient encounter. The physician may therefore request to review a co-pay or estimated out-of-pocket cost for the patient, and/or inventory information, to discuss with the patient and/or to consider, possibly before selecting a pharmacy to send the prescription. The request may be referred to as an order request, benefit request, prescription request, benefit coverage inquiry, prescription claim, and/or prescription transaction. A benefit request, prescription request, benefit coverage inquiry, prescription claim, and/or prescription transaction may be considered a specific type of order request and may include a request regarding prescription benefit coverage for a particular prescription entered by a physician, and/or information regarding a prescription transaction.

According to certain embodiments, the service provider computer 106 may receive and process the requests from the prescriber computer 118, regarding pricing estimates, inventory estimates, and/or the like relating to prescriptions provided by a physician and/or the like. The service provider computer 106 may additionally or alternatively receive and process requests from the pharmacy computer 112, such as prescription claims submitted in response to a patient obtaining the prescribed medication at the pharmacy.

The service provider computer 106 may transmit prescription claims to the payer computer 120 for adjudication. In this regard, the service provider computer 106 may transmit responses from the payer computer 120 to the prescriber computer 118 and/or pharmacy computer 112. For example, the service provider computer 106 may notify the prescriber computer 118 and/or pharmacy computer 112 of benefit coverage information and/or a benefit coverage response, such as but not limited to a co-pay or out-of-pocket costs to be paid by the patient for the prescription and/or the benefit applied to the prescription transaction. The response may include an estimate of a co-pay or out-of-pockets costs, such as in an example a response is not received from the payer computer 120, and/or the response may include an actual co-pay or out-of-pocket cost provided in a response from the payer computer 120. In certain embodiments, the service provider computer 106 and/or payer computer 120 may return a response such as a denial, or a response including indications such as prior approval required, and/or product not covered. Any of the aforementioned responses may be provided to the pharmacy computer 112 together with the prescription transaction response, or the service provider computer 106 may reformat the prescription transaction to include the details of such responses, and transmit the reformatted healthcare transaction to the pharmacy computer 112.

As described in further detail herein, the service provider computer 108 may access distribution data, such as may be stored on distribution database 105, such as via the distribution computer 104, to estimate inventory information pertaining to an order request and/or prescription request. In this regard, the estimated inventory information describing estimated inventory at a particular pharmacy, may be appended to or incorporated with a reformatted healthcare transaction intended for a prescriber computer 118. However, in certain embodiments, a message comprising the estimated inventory information may be transmitted to the prescriber computer 118 independently of any response from the payer computer 120, and/or independently of a pricing estimate or estimated benefit response provided by the service provider computer 106.

Figure 3:
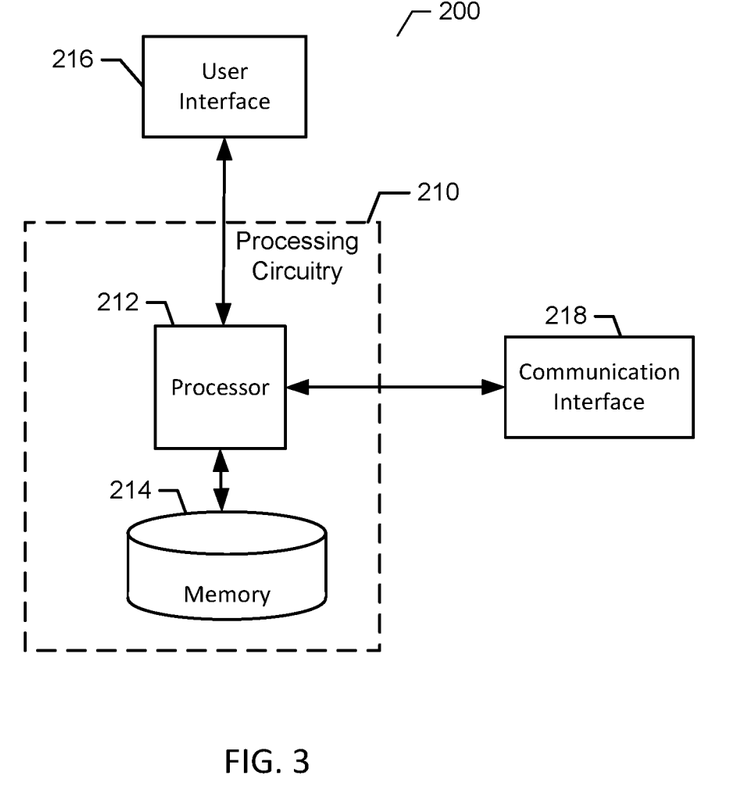
FIG. 3 is an exemplary schematic diagram of an apparatus in accordance with some example embodiments.

Referring now to FIG. 3, apparatus 200 is a computing device(s) configured for implementing merchant computer 102, distribution computer 104, distribution database 105, service provider computer 106, requesting computer 108, pharmacy computer 112, prescriber computer 118, and/or payer computer 120, according to example embodiments. Apparatus 200 may at least partially or wholly embody or be embodied by any of the merchant computer 102, distribution computer 104, distribution database 105, service provider computer 106, requesting computer 108, pharmacy computer 112, prescriber computer 118, and/or payer computer 120. Apparatus 200 may therefore implement any of the merchant computer 102, distribution computer 104, distribution database 105, service provider computer 106, requesting computer 108, pharmacy computer 112, prescriber computer 118, and/or payer computer 120, in accordance with some example embodiments, or may be implemented as a distributed system that includes any of the merchant computer 102, distribution computer 104, distribution database 105, service provider computer 106, requesting computer 108, pharmacy computer 112, prescriber computer 118, payer computer 120, and/or associated network(s).

It should be noted that the components, devices, and elements illustrated in and described with respect to FIG. 3 may not be mandatory and thus some may be omitted in certain embodiments. For example, FIG. 3 illustrates a user interface 216, as described in more detail below, which may be optional in some of the components of the systems of FIGS. 1 and 2. Additionally, some embodiments may include further or different components, devices, or elements beyond those illustrated in and described with respect to FIG. 3.

Continuing with FIG. 3, processing circuitry 210 may be configured to perform actions in accordance with one or more example embodiments disclosed herein. In this regard, the processing circuitry 210 may be configured to perform and/or control performance of one or more functionalities of apparatus 200 in accordance with various example embodiments. The processing circuitry 210 may be configured to perform data processing, application execution, and/or other processing and management services according to one or more example embodiments. In some embodiments apparatus 200, or a portion(s) or component(s) thereof, such as the processing circuitry 210, may be embodied as or comprise a circuit chip. The circuit chip may constitute means for performing one or more operations for providing the functionalities described herein.

In some example embodiments, the processing circuitry 210 may include a processor 212, and in some embodiments, such as that illustrated in FIG. 3, may further include memory 214. The processing circuitry 210 may be in communication with or otherwise control a user interface 216, and/or a communication interface 218. As such, the processing circuitry 210, such as that included in any of the merchant computer 102, distribution computer 104, distribution database 105, service provider computer 106, requesting computer 108, pharmacy computer 112, prescriber computer 118, payer computer 120, and/or apparatus 200 may be embodied as a circuit chip (e.g., an integrated circuit chip) configured (e.g., with hardware, software, or a combination of hardware and software) to perform operations described herein.

The processor 212 may be embodied in a number of different ways. For example, the processor 212 may be embodied as various processing means such as one or more of a microprocessor or other processing element, a coprocessor, a controller, or various other computing or processing devices including integrated circuits such as, for example, an ASIC (application specific integrated circuit), an FPGA (field programmable gate array), or the like. Although illustrated as a single processor, it will be appreciated that the processor 212 may comprise a plurality of processors. The plurality of processors may be in operative communication with each other and may be collectively configured to perform one or more functionalities of apparatus 200 as described herein. The plurality of processors may be embodied on a single computing device or distributed across a plurality of computing devices collectively configured to function as merchant computer 102, distribution computer 104, distribution database 105, service provider computer 106, requesting computer 108, pharmacy computer 112, prescriber computer 118, payer computer 120, and/or apparatus 200. In some example embodiments, the processor 212 may be configured to execute instructions stored in the memory 214 or otherwise accessible to the processor 212. As such, whether configured by hardware or by a combination of hardware and software, the processor 212 may represent an entity (e.g., physically embodied in circuitry—in the form of processing circuitry 210) capable of performing operations according to embodiments of the present invention while configured accordingly. Thus, for example, when the processor 212 is embodied as an ASIC, FPGA, or the like, the processor 212 may be specifically configured hardware for conducting the operations described herein. Alternatively, as another example, when the processor 212 is embodied as an executor of software instructions, the instructions may specifically configure the processor 212 to perform one or more operations described herein.

In some example embodiments, the memory 214 may include one or more non-transitory memory devices such as, for example, volatile and/or non-volatile memory that may be either fixed or removable. In this regard, the memory 214 may comprise a non-transitory computer-readable storage medium. It will be appreciated that while the memory 214 is illustrated as a single memory, the memory 214 may comprise a plurality of memories. The plurality of memories may be embodied on a single computing device or may be distributed across a plurality of computing devices. The memory 214 may be configured to store information, data, applications, computer program code, instructions and/or the like for enabling apparatus 200 to carry out various functions in accordance with one or more example embodiments. For example, when apparatus 200 is implemented as service provider computer 106, memory 214 may be configured to store computer program code for performing corresponding functions thereof, as described herein according to example embodiments.

Still further, memory 214 may be configured to store routing tables, that facilitate determining the destination of communications received from a merchant computer 102, distribution computer 104, requesting computer 108, pharmacy computer 112, prescriber computer 118, and/or payer computer 120. Memory 214 may further include reconciliation tables for tracking the order requests, prescription requests, prescription claims, and/or healthcare transactions received by the service provider computer 106, and reconciling them with corresponding responses received. The memory 214 may further comprise a database comprising distribution data, such as stored on distribution database 105.

The memory 214 may be further configured to buffer input data for processing by the processor 212. Additionally or alternatively, the memory 214 may be configured to store instructions for execution by the processor 212. In some embodiments, the memory 214 may include one or more databases that may store a variety of files, contents, or data sets. For example, order requests, prescription requests, prescription transactions, and/or prescription claims may be stored in memory 214 and modified as described herein. Accordingly, the memory 214 may be modified to reformat order requests, prescription requests, prescription claims, healthcare transactions, and/or the like with additional information received, determined and/or generated according to example embodiments.

Among the contents of the memory 214, applications may be stored for execution by the processor 212 to carry out the functionality associated with each respective application. In some cases, the memory 214 may be in communication with one or more of the processor 212, user interface 216, and/or communication interface 218, for passing information among components of apparatus 200.

The optional user interface 216 may be in communication with the processing circuitry 210 to receive an indication of a user input at the user interface 216 and/or to provide an audible, visual, mechanical, or other output to the user. As such, the user interface 216 may include, for example, a keyboard, a mouse, a display, a touch screen display, a microphone, a speaker, and/or other input/output mechanisms. As such, in embodiments in which apparatus 200 implemented as the prescriber computer 118, the user interface 216 may, in some example embodiments, provide means for user entry of prescription details, such as but not limited to an identifier of the prescribed medication, quantity, dosage, units of measure, days' supply, preferred pharmacy, and/or the like. The user interface 216 may be further configured to display estimated inventory information, such as when apparatus 200 is implemented as a prescriber computer 118. In some example embodiments, aspects of user interface 216 may be limited or the user interface 216 may not be present.

The communication interface 218 may include one or more interface mechanisms for enabling communication with other devices and/or networks. In some cases, the communication interface 218 may be any means such as a device or circuitry embodied in either hardware, or a combination of hardware and software that is configured to receive and/or transmit data from/to a network and/or any other device or module in communication with the processing circuitry 210. By way of example, the communication interface 218 may be configured to enable communication amongst any of merchant computer 102, distribution computer 104, distribution database 105, service provider computer 106, requesting computer 108, pharmacy computer 112, prescriber computer 118, payer computer 120, and/or apparatus 200 over a network. Accordingly, the communication interface 218 may, for example, include supporting hardware and/or software for enabling wireless and/or wireline communications via cable, digital subscriber line (DSL), universal serial bus (USB), Ethernet, or other methods.

A network, such as the network in which any of the systems of FIG. 1 or 2, or components thereof or components described herein may operate, (e.g., merchant computer 102, distribution computer 104, distribution database 105, service provider computer 106, requesting computer 108, pharmacy computer 112, prescriber computer 118, payer computer 120, apparatus 200, and/or the like) may include a local area network, the Internet, any other form of a network, or any combination thereof, including proprietary private and semi-private networks and public networks. The network may comprise a wired network and/or a wireless network (e.g., a cellular network, wireless local area network, wireless wide area network, some combination thereof, and/or the like).

Figure 4:
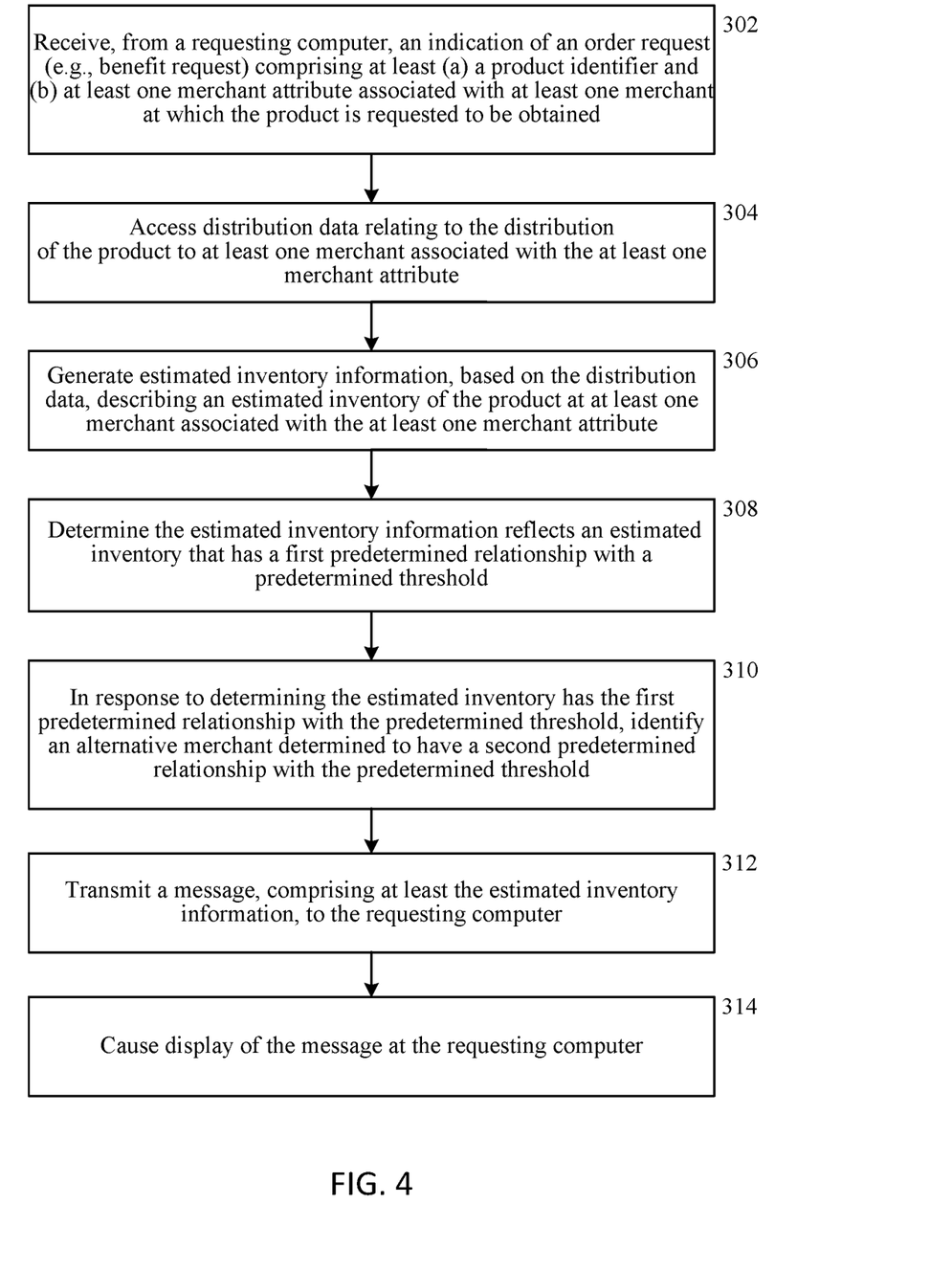
FIG. 4 is a flowchart of operations that may be performed in accordance with some example embodiments.

Having now described an example apparatus for implementing example embodiments, FIG. 4 is a flowchart illustrating example operations of an apparatus 200, according to some example embodiments. The operations of FIG. 4 may be performed by apparatus 200, such as with the service provider computer 106, and/or the like.

As shown by operation 302, apparatus 200 may include means, such as processor 212, memory 214, user interface 216, communication interface 218, and/or the like, for receiving, from a requesting computer, such as the requesting computer 108 and/or prescriber computer 118, an indication of an order request (e.g., benefit request) comprising at least (a) a product identifier and (b) a merchant attribute associated with at least one merchant at which the product is requested to be obtained. The product identifier may include any identifier of a product, such as a stock keeping unit (SKU), NDC, other prescription medication identifier, and/or the like. The product identifier may further include quantity, dosage, unit of measure, and/or days' supply.

The merchant attribute may include any information describing a merchant. For example, the merchant attribute may be information describing a geographical area (e.g., city, county, zip code, an entered or selected number of miles from an address or zip code, and/or any other information defining a geographical area). As another example, the merchant attribute may include an identifier, such as but not limited to a unique identifier of the merchant. In certain embodiments, the merchant attribute may include an identifier, such as but not limited to a unique identifier, of a merchant chain having multiple locations within a geographic area. In this regard, the at least one merchant attribute may include a merchant identifier and information defining a geographic area. For example, the at least one merchant attribute may include an identifier of the pharmacy chain "XYZ" and a zip code 17601, indicating a patient desires to obtain a certain prescription medication at a pharmacy belonging to the pharmacy chain "XYZ," in the zip code 17601. In certain embodiments, the merchant attribute may include an identifier of a pharmacy as defined in the National Provider Identifier (NPI) Standard. The identifier, or "NPI," may be a unique identification number of a health care provider and/or pharmacy. The merchant attribute may further comprise a National Council for Prescription Drug Programs (NCPDP) ID or identifier.

In this regard, the order request (e.g., benefit request) may be a prescription request entered by a physician or other practitioner via a prescriber computer 118. In certain embodiments, the order request may be included in, or associated with, a prescription claim and/or a benefit request to inquire regarding benefits associated with the prescription.

As shown by operation 304, apparatus 200 may include means, such as processor 212, memory 214, communication interface 218, and/or the like, for accessing distribution data relating to the distribution of the product to at least one merchant associated with the at least one merchant attribute. In this regard, the service provider computer 106 may access distribution data, such as on distribution database 105, optionally via the distribution computer 104. The service provider computer 106 and/or distribution computer 104 may access distribution data specific to the product identified in the order request (e.g., benefit request), and the merchant(s) indicated by the at least one merchant attribute of the order request. For example, the service provider computer 106 may access distribution data relating to the identified prescription medication, to all pharmacies in the pharmacy chain "XYZ" in the zip code 17601. In certain embodiments, the accessed distribution data may reflect certain data points incorporated in or associated with the product identifier, such as but not limited to unit of measure, dosage, quantify, days' supply, and/or the like.

In certain embodiments, if no distribution data is available for a certain merchant and/or pharmacy, and/or too little distribution data is available for the certain merchant and/or pharmacy (e.g., such that service provider computer 106 determines it cannot or should not generate estimated inventory information), example embodiments may be configured to identify other merchants and/or pharmacies having similar demographics to that of the certain merchant and/or pharmacy, such that the distribution data for another similar merchant and/or pharmacy can be considered in generating estimated inventory information for the certain merchant and/or pharmacy.

As shown by operation 306, apparatus 200 may include means, such as processor 212, memory 214, and/or the like, for generating estimated inventory information, based on the distribution data, describing an estimated inventory of the product at at least one merchant associated with the at least one merchant attribute. The estimated inventory information may comprise various indicators of estimated inventory levels, each in association with a merchant. For example, an indicator of an estimated inventory level may include low, medium, high, stock, low stock, out of stock, (or any other categorical descriptor of inventory level) an estimated number of days supply, an estimated quantity or units of the product, likelihood of the product being in stock (e.g., percentage or categorical descriptor), and/or any other descriptor of inventory level.

The indicator of the estimated inventory level may be determined in a variety of ways. For example, using the distributed quantity and frequency of a product to a particular merchant and/or pharmacy, example embodiments, such as with processor 212 and/or service provider computer 106, may generate an average quantity sold per day (or other time period), of the product by the merchant. Based on the last distribution date and amount, example embodiments may therefore calculate an estimated quantity available at the merchant as the distributed quantity–(average quantify sold per day×days lapsed since distribution).

As another example, a merchant and/or pharmacy having a repeat order placed every month for a certain product may be determined to have a low inventory in the last 5 days before a shipment, a high inventory in the first 10 days following a shipment, and a medium inventory for the days in between the periods of high and low inventory. Any number of categorical descriptions of the inventory, and any number of days associated with a respective categorical description of inventory may be used. For example, certain embodiments may determine a low inventory in the last 7 days prior to a shipment.

Such estimations may also be made based on distribution data that does not necessarily reflect a repeated or automated distribution request. For example, the service provider computer 106, such as with processor 212, may determine that distribution requests for a particular product and/or prescription medication by a merchant and/or pharmacy are placed as-needed, but may calculate the average number of days between each distribution request. In this regard, a next distribution request date may be estimated based on the last known distribution request. Example embodiments may therefore determine a low inventory as occurring during a predetermined number of days leading up to the estimated next distribution request.

In certain embodiments, the estimated inventory information may include an estimated date or timeline on which it is expected that a particular merchant and/or pharmacy has more product available, or when the product and/or prescription is in stock. For example, the estimated data may be the estimated or determined date of a next distribution.

As another example, the distribution data may relate to a distribution center for a chain of merchants and/or pharmacies, such that the distribution date to the individual merchants and/or pharmacies within the chain may be unknown. Example embodiments may make inferences accordingly, such as by estimating that the product and/or prescription medication is distributed to each merchant and/or pharmacy within the chain and in the distribution area, or geographic area, associated with the chain distribution center. In this regard, example embodiments account for the delay in time it may take for the product and/or prescription medication to reach the actual store locations.

The above described processes for generating estimated inventory information are provided merely as examples, and it will be appreciated that a variety of processes may be utilized for generating estimated inventory information.

In certain embodiments, the estimate inventory information may include an indication or message that a preferred pharmacy is out of stock or low in stock of a certain prescription medication with any of the specified quantify, unit of measure, dosage, and/or days' supply, but that the same prescription medication is available with a different quantify, unit of measure, dosage, and/or days' supply. This may be useful in certain embodiments as a physician prescribing 10 mg of a medication may be able to modify a prescription to 5 mg, and increased dosage, based on a preferred pharmacy's inventory.

It will be further appreciated that example embodiments may generate estimated inventory information for some or all merchants associated with the at least one merchant attribute indicated by the order request (e.g., benefit request). In certain embodiments, the service provider computer 106 may generate estimated inventory information for additional merchants and/or pharmacies, not associated with merchants and/or pharmacies associated with the at least one merchant attribute. For example, a physician entering an order request (e.g., benefit request) for a patient may select or indicate the patient's preferred pharmacy. As such, the order request (e.g., benefit request) may comprise one merchant attribute associated with the preferred pharmacy. However, according to certain embodiments, the service provider computer 106 may generate estimated inventory information for additional merchants and/or pharmacies, such as a nearby merchant and/or pharmacy (whether within a potential chain or outside of any potential chain), including one or more merchants and/or pharmacies not indicated in the order request (e.g., benefit request). As such, in certain embodiments, if the patient's preferred pharmacy is low or out of the prescribed medication, the service provider computer 106 may identify an alternative merchant identified as having a higher estimated inventory, or higher likelihood of having the prescribed medication in stock. In certain embodiments, service provider computer 106 may generate estimated inventory information for additional or alternative merchants and/or pharmacies only if it is determined the merchant(s) and/or pharmacy (or pharmacies) indicated by the order request (e.g., benefit request) has low inventory. An alternative merchant and/or pharmacy may be identified based on proximity to the merchant and/or pharmacy indicated in the order request (e.g., benefit request). For example, the alternative merchant and/or pharmacy may be the closest merchant and/or pharmacy to the merchant and/or pharmacy indicated in the order request, the closest merchant and/or pharmacy to the doctor, and/or a merchant and/or pharmacy in close proximity to the requesting computer 108 and/or physician associated therewith. In some examples, several next closest merchants and/or pharmacies may be identified, and respective estimated inventory information generated accordingly. It will be appreciated that other merchant attributes may be considered or may be weighted differently in determining an alternative merchant (s) and/or pharmacy (or pharmacies). For example, an order request (e.g., benefit request) may indicate that a particular merchant chain and/or pharmacy chain is important.

In any event, example embodiments may be configured to generate estimated inventory information for any number of merchants and/or pharmacies. In this regard, operations 304 and/or 306 may be repeated, to determine additional merchants and corresponding estimates that may be assessed in order to respond to the order request (e.g., benefit request) (described in further detail below).

As shown by operation 308, apparatus 200 may include means, such as processor 212, memory 214, and/or the like, for optionally determining the estimated inventory information reflects an estimated inventory that has a first predetermined relationship with a predetermined threshold. For example, the service provider computer 106 may determine the estimated inventory information is low, or equal to or less than a predetermined threshold number of days of remaining supply, equal to or less than a predetermined threshold remaining quantity, and/or the like. Any predetermined threshold may be used, and any predetermined relationship (e.g., less than, or less than or equal to) may be used. As another example, a predetermined relationship may include greater than, or greater than or equal to, such as in examples when estimated inventory information includes a likelihood of the product being sold out.

In this regard, as shown by operation 310, apparatus 200 may include means, such as processor 212, memory 214, and/or the like, for, in response to determining the estimated inventory has the first predetermined relationship with the predetermined threshold, identifying an alternative merchant determined to have a second predetermined relationship with the predetermined threshold. As set forth above, in certain embodiments, service provider computer 106 may identify alternative merchants and/or pharmacies in response to determining a preferred merchant and/or pharmacy has low inventory (or another first predetermined relationship with a predetermined threshold). In this regard, example embodiments may identify an alternative merchant and/or pharmacy that has a second predetermined relationship with the predetermined threshold, indicating the alternative merchant and/or pharmacy is likely to have the product in stock, and/or is more likely than another merchant and/or pharmacy (such as one identified based on the at least on merchant attribute) to have the product in stock. In this regard, if the first predetermined relationship includes less than, the second predetermined relationship may include greater than or equal to. Similarly, if the first predetermined relationship includes greater than, the second predetermined relationship may include less than or equal to.

As such, in operation 312, apparatus 200 may include means, such as processor 212, memory 214, communication interface 218, and/or the like, for transmitting a message, comprising at least the estimated inventory information, to the requesting computer. The estimated inventory information may be provided for any number of merchants and/or pharmacies, such as those associated with the merchant attribute(s) included in the order request (e.g., benefit request). For example, the message may include one or more alternative merchants and/or pharmacies, and respective estimated inventory information.

In operation 314, apparatus 200 may include means, such as processor 212, memory 214, user interface 216, communication interface 218, and/or the like, for causing display of the message at the requesting computer. The message may be displayed in real-time or near real-time relative to the receipt of the order request (e.g., benefit request) by the service provider computer 106. The term near real-time is referenced to account for short delays in processing time that may occur. In this regard, it will be appreciated that any of the operations described herein, such as but not limited to those provided in the flowchart of FIG. 4, may occur in real-time or near real-time in response to entry by the user of information pertaining to the order request (e.g., benefit request), such as by a user of the requesting computer 108 and/or prescriber computer 118.

The estimated inventory information, generated by the service computer 106, may be provided on a user interface of the requesting computer 108 and/or prescriber computer 118. As such, a user of the requesting computer 108, such as a physician or other prescriber, may view the estimated inventory information. A physician and/or the like may discuss with the patient a pharmacy that is convenient for the patient, and that is likely to have the prescribed medication in stock.

In certain embodiments, the estimated inventory information may be provided for informational purposes. In certain embodiments, a user of the requesting computer 108 and/or prescriber computer 118 may select a merchant and/or pharmacy indicated in the estimated inventory information, at which the product and/or prescribed medication is to be obtained. For example, the user (e.g. physician) may select the merchant (e.g., pharmacy) to which the prescription transaction should be submitted. The selection may be transmitted to the service provider computer 106 for further processing and/or routing. For example, once confirmed, the selected merchant and/or pharmacy may be indicated as a recipient of the order request (e.g., benefit request), prescription request, and/or prescription transaction. In certain embodiments, a prescription claim may be forwarded to the payer computer 120 for adjudication. In some embodiments, a prescription claim may be forwarded to the payer computer 120 when the order request (e.g., benefit request) is received in conjunction with operation 302, whether or not the pharmacy at which the prescription medication is to be obtained is known.

According to certain embodiments, the message provided to the prescriber computer 118 may further include information regarding prescription claim adjudication, co-pay and/or out-of-pocket cost estimates, and/or the like.

Example embodiments provided herein therefore provide a solution to the technical problem of enabling an order request (e.g., benefit request) to be submitted without notifying appropriate parties that the associated merchant and/or pharmacy is out of stock or low on stock. Despite engaging numerous computers to process such order requests, and/or benefit requests, and/or the like, prior systems do not alert requesting computers and/or prescriber computers of inventory at the time an order request, (e.g., benefit request) is submitted by the requesting computers and/or prescriber computers, and/or received by the service provider computer. Example embodiments provided herein provide a technical solution to the technical problem by accessing distribution data, generating estimated inventory information accordingly, and providing the estimated inventory information in real-time or near real-time to the requesting computer. Due to the complexities of the systems described herein, and the desire for real-time or near real-time estimated inventory information, technical challenges are presented with regard to generating such estimates, due to many factors outside of the control of the service provider. For instance, as set forth above, the service provider may not have access to information regarding actual inventory levels at various merchants and/or pharmacies, and/or may have limited distribution data available.

Therefore, example embodiments provide improvements to the existing technology of service provider computers, such as those that process prescription claims, prescription transactions, and/or the like.

The example embodiments provided herein may further improve functioning of the service provider computer 106, and other associated computers, by reducing the resources otherwise expended in conjunction with a submitted order request and/or benefit request for which an individual visits the merchant and/or pharmacy and discovers the product and/or prescribed medication is out of stock. In such scenarios, one order request and/or benefit request may need to be cancelled, so that a replacement order request and/or benefit request can be generated in its place. As such, example embodiments conserve processing resources and/or memory resources otherwise expended on the processing, communication, routing and storage of the cancelled order requests and/or benefit requests, and other related and/or downstream processes. For example, a forwarding of a prescription claim to payer computer 120 for adjudication, only for it to be later cancelled and resubmitted by the requesting computer 108 and/or prescriber computer 118 with a change in merchant and/or pharmacy, because the initially indicated merchant and/or pharmacy was out of stock, may waste processing resources and memory resources needed for routing and processing such claims. Additionally, the processing resources otherwise expended to route the order request (e.g., prescription order or benefit request) to the merchant or pharmacy that is low on inventory or out of stock, may be reduced, by preventing such order requests from being routed thereto. Example embodiments may reduce the expenditure of resources by providing estimated inventory information and therefore reducing the number of cancelled, and resubmitted order requests (e.g., benefit requests) that may occur due to a customer learning when visiting the merchant, that the merchant is out of inventory. By providing the estimated inventory information, a user of the requesting computer 108 and/or prescriber computer 118, can select a merchant and/or pharmacy that is determined to have the product and/or prescription medication in stock, or is likely to have the product and/or prescription medication in stock, and possibly avoid sending order requests and/or benefit requests to merchants or pharmacies having low or no stock.

Moreover, the provision of the estimated inventory information in real-time or near real-time to the requesting computer 108 and/or prescriber computer 118 provides a practical application of notifying users of the requesting computer 108 and/or prescriber computer 118 and associated parties, such as a patient, of estimated inventory at various merchants and/or pharmacies, even in instances in which the service provider computer 106 does not have access to actual inventory information of the requesting computer 108 and/or prescriber computer 118.

It will be appreciated that the figures are each provided as examples and should not be construed to narrow the scope or spirit of the disclosure in any way. In this regard, the scope of the disclosure encompasses many potential embodiments in addition to those illustrated and described herein. Numerous other configurations may also be used to implement embodiments of the present invention.

FIG. 4 illustrates operations of a method, apparatus, and computer program product according to some example embodiments. It will be understood that each operation of the flowchart or diagrams, and combinations of operations in the flowchart or diagrams, may be implemented by various means, such as hardware and/or a computer program product comprising one or more computer-readable mediums having computer readable program instructions stored thereon. For example, one or more of the procedures described herein may be embodied by computer program instructions of a computer program product. In this regard, the computer program product(s) which embody the procedures described herein may comprise one or more memory devices of a computing device (for example, memory 214) storing instructions executable by a processor in the computing device (for example, by processor 212). In some example embodiments, the computer program instructions of the computer program product(s) which embody the procedures described above may be stored by memory devices of a plurality of computing devices. As will be appreciated, any such computer program product may be loaded onto a computer or other programmable apparatus (for example, apparatus 200) to produce a machine, such that the computer program product including the instructions which execute on the computer or other programmable apparatus creates means for implementing the functions specified in the flowchart block(s). Further, the computer program product may comprise one or more computer-readable memories on which the computer program instructions may be stored such that the one or more computer-readable memories can direct a computer or other programmable apparatus to function in a particular manner, such that the computer program product may comprise an article of manufacture which implements the function specified in the flowchart block(s). The computer program instructions of one or more computer program products may also be loaded onto a computer or other programmable apparatus (for example, apparatus 200 and/or other apparatus) to cause a series of operations to be performed on the computer or other programmable apparatus to produce a computer-implemented process such that the instructions which execute on the computer or other programmable apparatus implement the functions specified in the flowchart block(s).

Accordingly, blocks of the flowchart support combinations of means for performing the specified functions and combinations of operations for performing the specified functions. It will also be understood that one or more blocks of the flowchart, and combinations of blocks in the flowchart, can be implemented by special purpose hardware-based computer systems which perform the specified functions, or combinations of special purpose hardware and computer instructions.

Many modifications and other embodiments of the inventions set forth herein will come to mind to one skilled in the art to which these inventions pertain having the benefit of the teachings presented in the foregoing descriptions and the associated drawings. Therefore, it is to be understood that the inventions are not to be limited to the specific embodiments disclosed and that modifications and other embodiments are intended to be included within the scope of the appended claims. Moreover, although the foregoing descriptions and the associated drawings describe example embodiments in the context of certain example combinations of elements and/or functions, it should be appreciated that different combinations of elements and/or functions may be provided by alternative embodiments without departing from the scope of the appended claims. In this regard, for example, different combinations of elements and/or functions than those explicitly described above are also contemplated as may be set forth in some of the appended claims. Although specific terms are employed herein, they are used in a generic and descriptive sense only and not for purposes of limitation.

That which is claimed:

1. An apparatus comprising at least one processor and at least one memory including computer program code, the at least one memory and the computer program code configured to, with the processor, cause the apparatus to at least:

receive, from a prescriber computer, an indication of an order request comprising at least (a) a product identifier and (b) at least one merchant attribute describing at least one merchant at which a product is requested to be obtained;

access distribution data relating to the distribution of product to at least one merchant associated with the at least one merchant attribute;

access prescription claims received via a communication interface and associated with the product identifier and the at least one merchant;

generate estimated inventory information, based on the distribution data and the prescription claims associated with the product identifier and the at least one merchant, wherein the estimated inventory information describes an estimated inventory of the product of at least one merchant associated with the at least one merchant attribute;

transmit a message, comprising at least the estimated inventory information and cost information, to the prescriber computer;

cause display of the message at the prescribing computer;

receive, from the prescriber computer, an indication of a selected merchant to which to route the order request; and in response to the indication of the selected merchant, transmit the order request to a pharmacy computer associated with the selected merchant.

2. The apparatus of claim 1, wherein the apparatus does not have access to actual inventory information of the at least one merchant.

3. The apparatus of claim 1, wherein the order request comprises a benefit request, the product identifier identifies a prescribed medication, and the at least one merchant attribute describes a pharmacy at which the prescribed medication is requested to be obtained.

4. The apparatus of claim 1, wherein the at least one memory and the computer program code are configured to, with the processor, cause the apparatus to at least:
   determine that the estimated inventory information reflects an estimated inventory that has a first predetermined relationship with a predetermined threshold; and
   in response to determining that the estimated inventory has the first predetermined relationship with the predetermined threshold, identify an alternative merchant determined to have a second predetermined relationship with the predetermined threshold, wherein the message further comprises an indication of the alternative merchant.

5. The apparatus of claim 1, wherein the distribution data comprises at least one of a last distribution date and average distribution frequency, and the estimated inventory information is determined based on at least the last distribution date and the average distribution frequency.

6. The apparatus of claim 1, wherein the at least one merchant attribute is a merchant identifier of the merchant at which the product is requested to be obtained.

7. The apparatus of claim 1, wherein the at least one merchant attribute describes a geographic area of the merchant at which the product is requested to be obtained.

8. A method comprising:
   receiving, from a prescriber computer, an indication of an order request comprising at least (a) a product identifier and (b) at least one merchant attribute describing at least one merchant at which a product is requested to be obtained;
   accessing distribution data relating to the distribution of the product to at least one merchant associated with the at least one merchant attribute;
   accessing prescription claims received via a communication interface and associated with the product identifier and the at least one merchant;
   generating estimated inventory information, based on the distribution data and the prescription claims associated with the product identifier and the at least one merchant, wherein the estimated inventory information describes an estimated inventory of the product of at least one merchant associated with the at least one merchant attribute;
   transmitting a message, comprising at least the estimated inventory information and cost information, to the prescriber computer;
   causing display of the message at the prescriber computer;
   receiving, from the prescriber computer, an indication of a selected merchant to which to route the order request; and
   in response to the indication of the selected merchant, transmitting the order request to a pharmacy computer associated with the selected merchant.

9. The method of claim 8, wherein the method does not have access to actual inventory information of the at least one merchant.

10. The method of claim 8, wherein the order request comprises a benefit request, the product identifier identifies a prescribed medication, and the at least one merchant attribute describes a pharmacy at which the prescribed medication is requested to be obtained.

11. The method of claim 8, further comprising:
   determining that the estimated inventory information reflects an estimated inventory that has a first predetermined relationship with a predetermined threshold; and
   in response to determining that the estimated inventory has the first predetermined relationship with the predetermined threshold, identifying an alternative merchant determined to have a second predetermined relationship with the predetermined threshold, wherein the message further comprises an indication of the alternative merchant.

12. The method of claim 8, wherein the distribution data comprises at least one of a last distribution date and average distribution frequency, and the estimated inventory information is determined based on at least the last distribution date and the average distribution frequency.

13. The method of claim 8, wherein the at least one merchant attribute is a merchant identifier of the merchant at which the product is requested to be obtained.

14. The method of claim 8, wherein the at least one merchant attribute describes a geographic area of the merchant at which the product is requested to be obtained.

15. A computer program product comprising at least one non-transitory computer-readable storage medium having computer-executable program code instructions stored therein, the computer-executable program code instructions comprising program code instructions to:
   receive, from a prescriber computer, an indication of an order request comprising at least (a) a product identifier and (b) at least one merchant attribute describing at least one merchant at which a product is requested to be obtained;
   access distribution data relating to the distribution of the product to at least one merchant associated with the at least one merchant attribute;
   access prescription claims received via a communication interface and associated with the product identifier and the at least one merchant;
   generate estimated inventory information, based on the distribution data and the prescription claims associated with the product identifier and the at least one merchant, wherein the estimated inventory information describe an estimated inventory of the product of at least one merchant associated with the at least one merchant attribute;
   transmit a message, comprising at least the estimated inventory information, to the prescriber computer;
   cause display of the message at the prescriber computer;
   receive, from the prescriber computer, an indication of a selected merchant to which to route the order request; and
   in response to the indication of the selected merchant, transmit the order request to a pharmacy computer associated with the selected merchant.

16. The computer program product of claim 15, wherein the computer program product does not have access to actual inventory information of the at least one merchant.

17. The computer program product of claim 15, wherein the order request comprises a benefit request, the product identifier identifies a prescribed medication, and the at least one merchant attribute describes a pharmacy at which the prescribed medication is requested to be obtained.

18. The computer program product of claim 15, wherein the computer-executable program code instructions further comprise program code instructions to:

determine that the estimated inventory information reflects an estimated inventory that has a first predetermined relationship with a predetermined threshold; and in response to determining that the estimated inventory has the first predetermined relationship with the predetermined threshold, identify an alternative merchant determined to have a second predetermined relationship with the predetermined threshold, wherein the message further comprises an indication of the alternative merchant.

* * * * *